US00PP22086P3

(12) United States Plant Patent
Egger

(10) Patent No.: US PP22,086 P3
(45) Date of Patent: Aug. 16, 2011

(54) ***AGASTACHE* PLANT NAMED 'SUMMER FIESTA'**

(50) Latin Name: ***Agastache* spp.**
Varietal Denomination: Summer Fiesta

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 45 days.

(21) Appl. No.: 12/653,640

(22) Filed: Dec. 14, 2009

(65) Prior Publication Data

US 2011/0145959 P1 Jun. 16, 2011

(51) Int. Cl.
*A01H 5/00* (2006.01)

(52) U.S. Cl. ..... Plt./399

(58) Field of Classification Search ..... Plt./399
See application file for complete search history.

(56) References Cited

U.S. PATENT DOCUMENTS

PP20,371 P2 * 9/2009 Egger ..... Plt./399

* cited by examiner

*Primary Examiner* — Wendy C Haas
(74) *Attorney, Agent, or Firm* — Klarquist Sparkman, LLP

(57) ABSTRACT

A new and distinct form of *Agastache* plant characterized by red flowers, large, dense flower spikes, an upright branching habit, a long bloom time, and excellent vigor.

1 Drawing Sheet

Botanical denomination: *Agastache* spp.
Variety designation: 'Summer Fiesta'.
Parentage: *Agastache* 'Raspberry Summer' (U.S. Plant Pat. No. 20,371)×unknown.

BACKGROUND OF THE INVENTION

The present invention relates to a new and distinct cultivar of *Agastache,* given the name, 'Summer Fiesta'. *Agastache* is in the family Lamiaceae. This new variety is an open pollinated seedling selection out of *Agastache* 'Raspberry Summer' as such the pollen parent is unknown.

Compared to the seed parent, *Agastache* 'Raspberry Summer' (U.S. Plant Pat. No. 20,371), the new cultivar has red rather than red purple flowers.

Compared to *Agastache* 'Acapulco Orange', the new cultivar has redder flowers with longer inflorescences.

This plant exhibits the following characteristics that make it unique:

1. red flowers,
2. large, dense flower spikes,
3. an upright branching habit,
4. a long bloom time, and
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows close up of a nine-month-old *Agastache* 'Summer Fiesta' growing in the field in late summer in Canby, Oreg.

FIG. 2 shows a bed of nine-month-old *Agastache* 'Summer Fiesta' growing in the field in late summer in Canby, Oreg.

DETAILED PLANT DESCRIPTION

The following is a detailed description of the new *Agastache* cultivar based on observations of eighteen-month-old specimens in August grown outside in the ground in the trial beds in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form.*—Upright.
*Type.*—Herbaceous perennial.
*Cold hardiness.*—USDA Zone 7-10.
*Size.*—Grows to 40 cm wide and 70 cm tall to the top of the flowers.
*Vigor.*—Excellent.
*Branching.*—About 9 main branches from the base.
*Stem.*—Square in cross section, grows to 7 mm wide and 30 cm tall to the first flower, sparsely pubescent, internodes range from 2 to 8 cm long, Yellow Green 146C.
*Roots.*—White 155B, fibrous, plants root easily from stem tip cuttings.

Leaf:

*Type.*—Simple.
*Arrangement.*—Opposite.
*Shape.*—Ovate.
*Venation.*—Pinnate.
*Margins.*—Crenate to serrate.
*Apex.*—Acute.
*Base.*—Truncate to cordate.
*Blade size.*—Grows to 50 mm long and 30 mm wide.
*Surface texture.*—Very short hairs on bottom side, glabrous top side.

*Petiole description.*—22 mm long and 1 mm wide, pubescent, Yellow Green 147B.

*Leaf color.*—Top side closest to Green N137A, bottom side closest to Yellow Green 147B.

Inflorescence:

*Type.*—Terminal spike with 7 to 14 whorls.

*Number of flowers.*—Up to 220 per spike.

*Size of inflorescence.*—Grows to 41 cm tall and 7 cm wide.

*Peduncle.*—Grows to 46 cm tall and 3 mm wide, pubescent, Yellow Green 146C.

*Pedicel.*—2 to 3 mm long, pubescent, Yellow Green 146C in shade and tinted Greyed Purple 187B in sun.

*Bloom period.*—July through frost in Canby, Oreg.

Flower bud:

*Size.*—21 mm long and 4 mm wide at the widest point prior to opening.

*Description.*—Tubular.

*Surface texture.*—Pubescent.

*Color.*—Red 51A.

Flower:

*Type.*—Zygomorphic.

*Shape.*—Bilabiate, tubular.

*Size.*—30 mm long and 7 mm wide.

*Corolla description.*—22 mm long and spreads to 7 mm wide; color outside Red 39A and inside Red 50A to 50B; pubescent inside and out, tube 20 mm long and 1 mm to 4 mm wide; 2 upper lobes joined 3 mm long and 2 mm wide, ovate, acute, entire; three lower lobes, two spreading sideways and curve down slightly, each 2.5 mm long and 2.5 mm wide, acute, entire; the bottom lobe broad, reflexed, obovate, notched at the tip, entire, 4 mm wide and 4 mm deep.

*Calyx description.*—6 mm long and 2.5 mm wide, pubescent outside and glabrous inside, 5 lobed, lobes narrow, 2 mm long, entire, acuminate, color closest to Brown 200D.

*Pistil description.*—30 mm long, ovary 0.5 mm long, Yellow Green 146C, style 19.5 mm long, White NN155D; stigma two-parted, 1 mm, Red Purple 71A.

*Stamen description.*—4 in number, paired and exerted, top two 10 mm long and bottom two 8 mm long, filaments Red Purple 71C, anthers 0.5 mm long, Red Purple 71C, pollen White 155A.

*Fragrance.*—Light herbal.

*Lastingness.*—A spike blooms for about 3 weeks on the plant.

Fruit/seed: 4 nutlets, 1 mm long, ovoid, Black 202A

Pests and diseases: *Agastache* are known to be susceptible to downy mildew (*Peronospora*) and rust (*Puccinia*) in dry summer months. The new cultivar has no known resistances but has shown no problems in Canby, Oreg.

I claim:

1. A new and distinct form of *Agastache* plant substantially as shown and described.

* * * * *

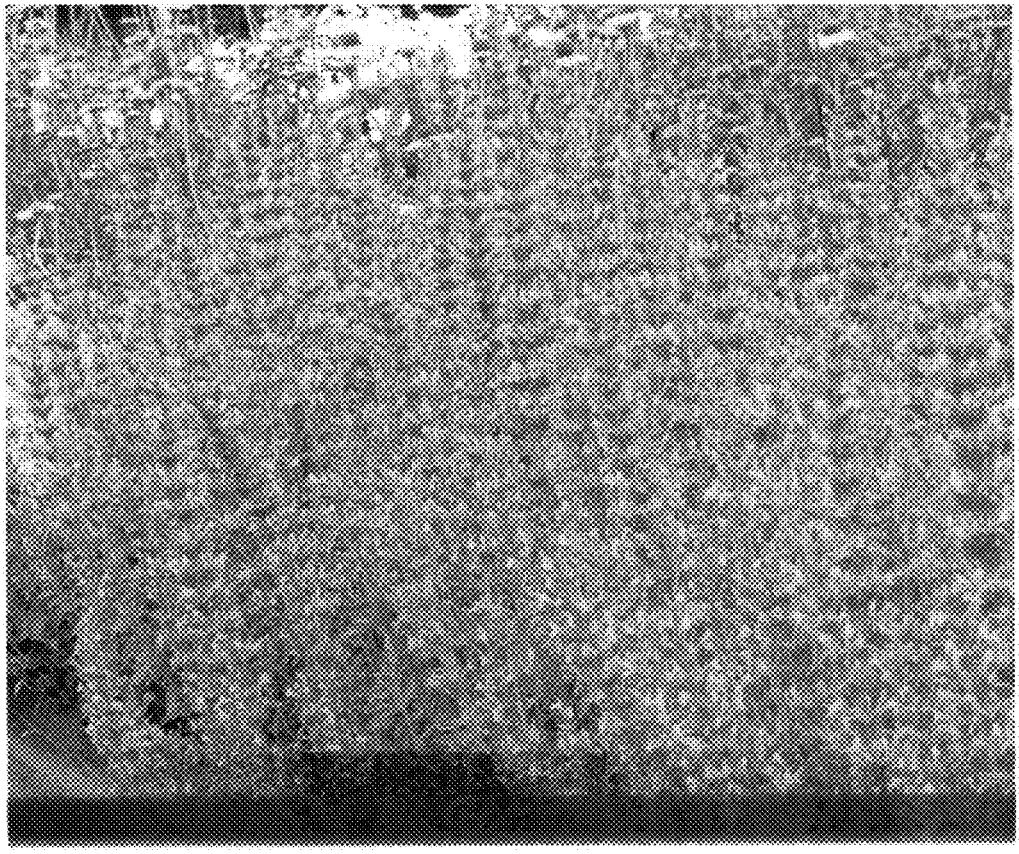

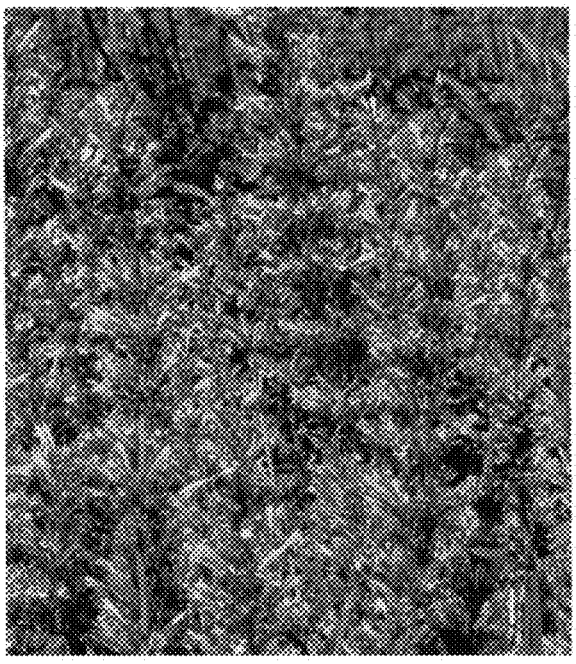
FIG. 1 above
FIG. 2 below